United States Patent [19]
Sakamoto et al.

[11] Patent Number: 5,990,106
[45] Date of Patent: Nov. 23, 1999

[54] BICYCLIC AMINO GROUP-SUBSTITUTED PYRIDONECARBOXYLIC ACID DERIVATIVES, ESTERS THEREOF AND SALTS THEREOF, AND BICYCLIC AMINES USEFUL AS INTERMEDIATES THEREOF

[75] Inventors: Masato Sakamoto, Toyonaka; Katsumi Chiba, Osaka; Yukio Tominaga, Toyonaka; Akira Minami, Hirakata, all of Japan

[73] Assignee: Dainippon Pharmaceutical Co., Ltd., Osaka, Japan

[21] Appl. No.: 08/875,728

[22] PCT Filed: Feb. 2, 1995

[86] PCT No.: PCT/JP95/00135

§ 371 Date: Aug. 4, 1997

§ 102(e) Date: Aug. 4, 1997

[87] PCT Pub. No.: WO95/21163

PCT Pub. Date: Aug. 10, 1995

[51] Int. Cl.$^6$ .......................... A61K 31/47; A61K 31/40; C07D 209/52; C07D 401/04

[52] U.S. Cl. .......................... 514/248; 514/258; 514/267; 514/291; 514/293; 514/296; 514/300; 514/312; 514/412; 544/234; 544/235; 544/236; 544/238; 544/250; 544/279; 546/80; 546/83; 546/89; 546/92; 546/123; 546/156; 548/515

[58] Field of Search ...................... 514/248, 258, 514/267, 291, 293, 296, 300, 312, 412; 544/234, 235, 236, 238, 250, 279; 546/80, 83, 89, 92, 123, 156; 548/515

[56] References Cited

FOREIGN PATENT DOCUMENTS

| 0 022 288 | 1/1981 | European Pat. Off. . |
| 0 343 524 | 11/1989 | European Pat. Off. . |
| 0 413 455 | 2/1991 | European Pat. Off. . |
| 0 550 019 | 7/1993 | European Pat. Off. . |
| 56-11729 | 2/1981 | Japan . |
| 64-056673 | 3/1989 | Japan . |
| WO94/15933 | 7/1994 | WIPO . |

OTHER PUBLICATIONS duPont, *Chem. Abstr.*, vol. 66 (1967) p 3554, Abstract No. 37500b.

Chiba et al., *Chem. Abstr.*, vol. 111, No. 17, Oct. 23, 1989 Abstract No. 111–153779w.

*Primary Examiner*—Mukund J. Shah
*Assistant Examiner*—Brenda Coleman
*Attorney, Agent, or Firm*—Wenderoth, Lind & Ponack, L.L.P.

[57] ABSTRACT

This invention relates to bicyclic amino group-substituted pyridonecarboxylic acid derivatives of the general formula A—Pri esters thereof and salts thereof, wherein: Pri is a pyridonecarboxylic acid residue, and A is a bicyclic amino group represented by the following formula and joined to the 7-position of the pyridonecarboxylic acid or a position equivalent to the 7-position thereof.

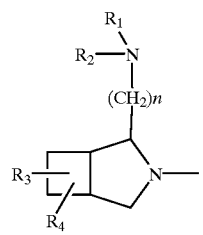

wherein $R_1$ and $R_2$ may be the same or different and each represents a hydrogen atom, a lower alkyl group or an amino-protecting group; $R_3$ and $R_4$ may be the same or different and each represents a hydrogen atom, a halogen atom, a cyano group, a hydroxyl group, an oxo group, a lower alkoxy group or a lower alkyl group; and n is an integer of 0 or 1.

The above-described pyridonecarboxylic acid derivatives, esters thereof and salts thereof are useful as antibacterial agents.

This invention also relates to bicyclic amine compounds useful as direct intermediates for the synthesis of the above-described pyridonecarboxylic acid derivatives.

8 Claims, No Drawings

BICYCLIC AMINO GROUP-SUBSTITUTED PYRIDONECARBOXYLIC ACID DERIVATIVES, ESTERS THEREOF AND SALTS THEREOF, AND BICYCLIC AMINES USEFUL AS INTERMEDIATES THEREOF

CROSS-REFERENCE TO RELATED APPLICATION

This application is a 371 of PCT/JP95/00135, filed Feb. 2, 1995.

TECHNICAL FIELD

This invention relates to novel compounds useful as antibacterial agents, and bicyclic amines useful as intermediates for the synthesis thereof.

BACKGROUND ART

A variety of antibacterial pyridonecarboxylic acid derivatives are known. For example, Japanese Patent Application Laid-Open No. 56673/'89 describes pyridonecarboxylic acids of the general formula

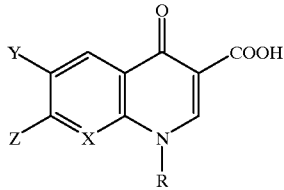

(A)

wherein R represents a lower alkyl group, a halogenated lower alkyl group, a lower alkenyl group, a cycloalkyl group, or a phenyl group which may have one or more substituents; X represents a nitrogen atom or C—A in which A represents a hydrogen atom or a halogen atom; Y represents a hydrogen atom or a halogen atom; and Z represents a group of the formula

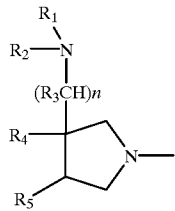

in which $R_1$ represents a hydrogen atom, a lower alkyloxy-carbonyl group, or an acyl group that may be substituted by one or more halogen atoms; two of $R_2$, $R_3$, $R_4$ and $R_5$ are connected directly or through a lower alkyl chain to form a ring, and the others represent hydrogen atoms; and n is 0 or 1, provided that $R_{25}$ and $R_3$ are directly connected. However, no specific example of a compound of the above formula (A) in which $R_4$ and $R_5$ are connected through an ethylene chain to form a ring is disclosed therein.

Moreover, European Patent Application Laid-Open No. 0343524 discloses pyridonecarboxylic acid derivatives of the general formula

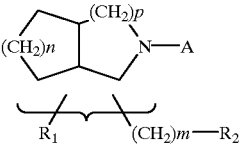

(B)

wherein $R_1$ is hydrogen, hydroxy, $C_1$–$C_4$ alkyl, $C_1$–$C_4$ alkoxy, oxo, halogen, or amino which may optionally be substituted by $C_1$–$C_4$ alkyl and/or $C_1$–$C_4$ alkanoyl; $R_2$ is azido, hydroxy, $C_1$–$C_4$ alkoxy, $C_1$–$C_4$ alkoxycarbonyl, $C_1$–$C_4$ alkanoyl, or amino which may optionally be substituted by $C_1$–$C_4$ alkyl and/or $C_1$–$C_4$ alkanoyl: A is

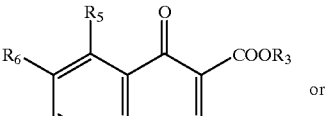

or

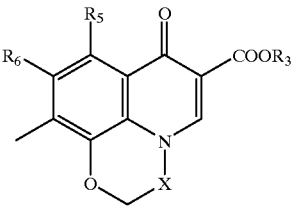

$R_3$ is hydrogen or a carboxyl-protecting group; $R_4$ is $C_1$–$C_4$ alkyl, $C_2$–$C_5$ alkenyl, $C_3$–$C_5$ cycloalkyl, mono- or difluorophenyl, or a five-membered or six-membered heterocyclic group which may optionally be substituted by halogen and/or $C_1$–$C_4$ alkyl; $R_5$ is hydrogen, amino, hydroxy or $C_1$–$C_4$ alkoxy; $R_6$ is halogen: X is CH–($C_1$—$C_4$ alkyl), C=$CH_2$, N—H or N—($C_1$–$C_4$ alkyl); Z is CQ or N; Q is hydrogen, $C_1$–$C_4$ alkoxy, halogen, $C_1$–$C_4$ alkyl or cyano; m is an integer of 0 or 1; and n and p are each an integer of 1 to 3. However, they do not include any compound in which n is 0.

Furthermore, Chemical Abstract, 66, 37500b (1967) and Japanese Patent Application Laid-Open No. 11729/'81 disclose compounds of the formula

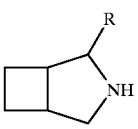

wherein R represents a hydrogen atom or a carboxyl group.

Conventional pyridonecarboxylic acid derivatives substituted by a bicyclic amino group, such as those represented by the above general formulae (A) and (B), are useful as antibacterial agents. However, their antibacterial activities and, in particular, in vivo antibacterial activities are not always satisfactory.

The present invention has been completed as a result of extensive investigations conducted with a view to developing a pyridonecarboxylic acid derivative showing a further enhancement in antibacterial activity and, in particular, in vivo antibacterial activity.

DISCLOSURE OF THE INVENTION

According to the present invention, there are provided novel bicyclic amino group-substituted pyridonecarboxylic acid derivatives of the general formula (I)

A—Pri    (I), esters thereof and salts thereof, wherein:

Pri is a pyridonecarboxylic acid residue, and

A is a bicyclic amino group represented by the following formula (C) and joined to the 7-position of the pyridonecarboxylic acid or a position equivalent to the 7-position thereof.

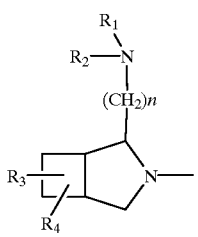

(C)

wherein $R_1$ and $R_2$ may be the same or different and each represents a hydrogen atom, a lower alkyl group or an amino-protecting group; $R_3$ and $R_4$ may be the same or different and each represents a hydrogen atom, a halogen atom, a cyano group, a hydroxyl group, an oxo group, a lower alkoxy group or a lower alkyl group; and n is an integer of 0 or 1.

According to the present invention, there are also provided bicyclic amine compounds of the following general formula (III) and salts thereof which are useful as intermediates for the synthesis of pyridonecarboxylic acid derivatives of the general formula (I).

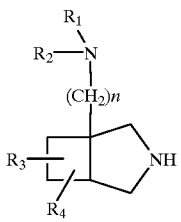

(III)

wherein $R_1$, $R_2$, $R_3$, $R_4$ and n have the same meanings as described previously.

The pyridonecarboxylic acid residue represented herein by "Pri" is a group having a skeletal structure of the following formula (D) in the molecule.

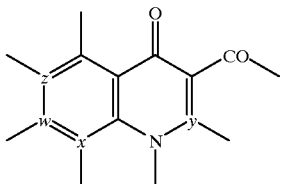

(D)

wherein x, y and z may be the same or different and each represents a carbon atom or a nitrogen atom, and w represents a carbon atom.

"The 7-position of the pyridonecarboxylic acid or a position equivalent to the 7-position thereof" means the position of w in the above formula (D). For example, this means the 7-position in pyridonecarboxylic acids having the quinoline or 1,8-naphthyridine structure, the 2-position in pyridonecarboxylic acids having the pyrido[2,3-d] pyrimidine structure, and the 10-position in pyridonecarboxylic acids having the ofloxacin structure.

Accordingly, the present invention preferably provides bicyclic amino group-substituted pyridonecarboxylic acid derivatives of the following general formula (I-A), esters thereof and salts thereof.

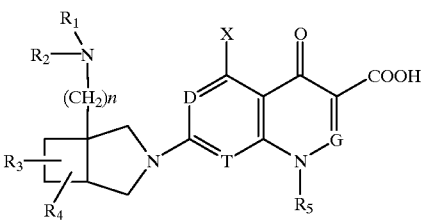

(I-A)

wherein $R_5$ represents a lower alkyl group, a lower alkenyl group, a lower cycloalkyl group, a phenyl group or a heterocyclic group (all of which may further be substituted); G represents C—E or a nitrogen atom in which E represents a hydrogen atom or combines with $R_5$ to form a bridge represented by the formula —S—CH(CH$_3$)—; T represents C—Z or a nitrogen atom in which Z represents a hydrogen atom, a halogen atom, a cyano group, a lower alkoxy group, a halogenated lower alkoxy group, a lower alkyl group or a halogenated lower alkyl group, or combines with $R_5$ to form a bridge represented by the formula —O—CH$_2$—CH(CH$_3$)—; X represents a hydrogen atom, a halogen atom, a hydroxyl group, a lower alkyl group or an amino group which may be protected; D represents C—Y or a nitrogen atom in which Y represents a hydrogen atom or a halogen atom; and $R_1$, $R_2$, $R_3$, $R_4$ and n have the same meanings as described previously.

The compounds (I) of the present invention are structurally characterized by the fact that a specific bicyclic amino group is chosen as a substituent joined to the 7-position of the pyridonecarboxylic acid or a position equivalent to the 7-position thereof.

The terms as used herein in connection with substituents and the like are described below.

Although no particular limitation is placed on the scope of the term "halogen atom", fluorine, chlorine and bromine are preferred. The term "lower" means groups containing 1 to 7 carbon atoms, unless otherwise specified. The term "lower alkyl" comprehends, for example, straight-chain and branched alkyl groups such as methyl, ethyl, propyl, isopropyl, butyl, t-butyl and pentyl, of which methyl is preferred. The term "lower alkenyl" comprehends, for example, vinyl, allyl, 1-propenyl and isopropenyl, of which vinyl is preferred. The term "lower cycloalkyl" comprehends, for example, cyclopropyl, cyclobutyl, cyclopentyl and cyclohexyl, of which cyclopropyl is preferred. The term "lower alkoxy" comprehends, for example, methoxy and ethoxy.

In the definition of $R_5$, examples of the substituent(s) used in the "lower alkyl group which may further be substituted", the "lower alkenyl group which may further be substituted", or the "lower cycloalkyl group which may further be substituted" include halogen atoms such as fluorine and chlorine. Examples of the substituent(s) used in the "phenyl group which may further be substituted" include halogen, lower alkyl, lower alkoxy, hydroxy, nitro and amino. The term "heterocyclic group" as used in the definition of $R_5$ comprehends, for example, five-membered and six-membered heterocyclic groups having N, O or S as a heteroatom, such as pyrrole, furan, thiophene, thiazole, isothiazole, oxazole, isoxazole, pyrazole, imidazole, pyridine, pyridazine, pyrimidine and pyrazine. The heterocyclic groups may further be substituted, for example, by halogen, lower alkyl, lower alkoxy, hydroxy, nitro and/or amino.

As the "protecting group" or "amino-protecting group" used in the "amino group which may be protected", there may be employed any of various groups which can readily be eliminated by a common deprotection reaction such as hydrolysis or hydrogenolysis, without exerting any substantial influence on the other structural part.

Examples of easily hydrolyzable amino-protecting groups which can readily be eliminated by hydrolysis include oxycarbonyl groups such as ethoxycarbonyl, t-butoxycarbonyl (abbreviated as Boc), benzyloxycarbonyl, p-methoxybenzyloxycarbonyl, vinyloxycarbonyl and β-(p-toluenesulfonyl)ethoxycarbonyl; acyl groups such as formyl, acetyl and trifluoroacetyl; and o-nitrophenylsulfenyl, trimethylsilyl, tetrahydropyranyl and diphenylphosphinyl.

Examples of easily hydrogenolyzable amino-protecting groups which can readily be eliminated by hydrogenolysis include arylsulfonyl groups such as p-toluenesulfonyl; phenyl- or benzyloxy-substituted methyl groups such as benzyl, trityl and benzyloxymethyl; arylmethoxycarbonyl groups such as benzyloxycarbonyl and o-methoxybenzyloxycarbonyl; and halogenoethoxycarbonyl groups such as β,β,β-trichloroethoxycarbonyl and β-iodoethoxycarbonyl.

"Esters" should preferably be those which can be converted into the corresponding free carboxylic acids (I) of the present invention by chemical or enzymological means. The esters which can be converted into the corresponding free carboxylic acids by chemical means such as hydrolysis include, for example, lower alkyl esters such as methyl esters and ethyl esters. The esters which can be converted into the corresponding free carboxylic acids not only by chemical means but also by enzymological means include, for example, lower alkanoyloxy-lower alkyl esters such as acetoxymethyl esters, 1-acetoxyethyl esters and pivaloyloxymethyl esters; lower alkoxycarbonyloxy-lower alkyl esters such as 1-ethoxycarbonyloxyethyl esters; aminoethyl esters such as 2-dimethylaminoethyl esters and 2-(1-piperidinyl)ethyl esters; and other esters such as 3-butyrolactonyl esters, choline esters, phthalidyl esters and (5-methyl-2-oxo-1,3-dioxol-4-yl)methyl esters.

As the salts of the compounds (I) of the present invention, pharmaceutically acceptable salts thereof are especially preferred. Examples thereof include salts formed with organic acids such as trifluoroacetic acid, acetic acid, lactic acid, succinic acid, methanesulfonic acid, maleic acid, malonic acid, gluconic acid and amino acids (e.g., aspartic acid and glutamic acid); salts formed with inorganic acids such as hydrochloric acid and phosphoric acid; metallic salts such as sodium, potassium, zinc and silver salts; ammonium salts; and salts formed with organic bases such as trimethylamine, triethylamine and N-methylmorpholine.

Salts of the compounds (III) of the present invention which are useful as intermediates include salts formed with inorganic acids such as hydrochloric acid and sulfuric acid; and salts formed with organic acids such as formic acid, acetic acid, trifluoroacetic acid, methanesulfonic acid and p-toluenesulfonic acid.

The compounds (I) and (III) of the present invention may sometimes exist in the form of hydrates and solvates. Moreover, they may exist in the form of optical isomers and stereoisomers (cis- and trans-forms). These compounds are also within the scope of the present invention.

Preferred examples of the compounds (I) of the present invention are the compounds represented by the following general formula (I-B).

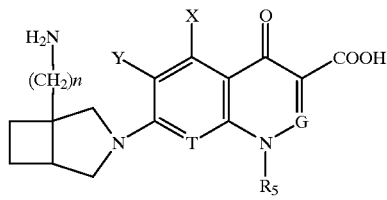

(I-B)

wherein $R_5$, G, T, X, Y and n have the same meanings as described previously.

More preferred examples of the compounds (I) of the present invention are the compounds represented by the following general formula (I-C).

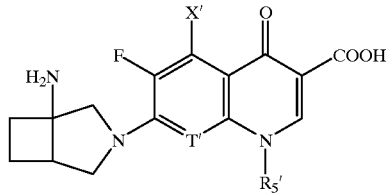

(I-C)

wherein $R_5'$ is a cyclopropyl group which may be substituted by fluorine, a 2,4-difluorophenyl group or a t-butyl group, X' is a hydrogen atom, a halogen atom or an amino group, and T' is CH, CF, CCl, C—OCH$_3$, C—OCHF$_2$ or a nitrogen atom.

More specific examples thereof are the compounds described in the Examples which will be given later.

The following compounds and physiologically acceptable salts thereof are also preferred examples of the compounds (I) of the present invention.

7-(1-Amino-3-azabicyclo[3.2.0]hept-3-yl)-8-cyano-1-cyclopropyl-6-fluoro-1,4-dihydro-4-oxoquinoline-3-carboxylic acid.

7-(1-Amino-3-azabicyclo[3.2.0]hept-3-yl)-8-bromo-1-cyclopropyl-6-fluoro-1,4-dihydro-4-oxoquinoline-3-carboxylic acid.

7-(1-Amino-3-azabicyclo[3.2.0]hept-3-yl)-1-cyclopropyl-6-fluoro-1,4-dihydro-8-methyl-4-oxoquinoline-3-carboxylic acid.

7-(1-Amino-3-azabicyclo[3.2.0]hept-3-yl)-1-cyclopropyl-6-fluoro-1,4-dihydro-4-oxo-8-trifluoromethylquinoline-3-carboxylic acid.

The compounds (I) of the present invention may be prepared, for example, by the following (a) amination reaction, (b) hydrolysis reaction and (c) ring closure reaction.

(a) Amination Reaction

The compounds (I) of the present invention, esters thereof and salts thereof may readily be prepared by reacting a compound of the general formula (II)

$$L\text{—Pri} \tag{II}$$

wherein Pri has the same meaning as described previously, L is a leaving group joined to Pri at the 7-position of Pri or a position equivalent to the 7-position thereof, and the carboxyl and oxo groups present in the pyridonecarboxylic acid residue represented by Pri may form a boron chelate bond therebetween, an ester thereof or a salt thereof with a bicyclic amine compound of the general formula (III)

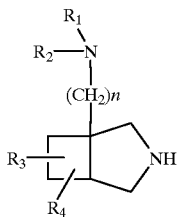

(III)

wherein $R_1$, $R_2$, $R_3$, $R_4$ and n have the same meanings as described previously; and if a boron chelate part is present in the product, hydrolyzing it.

Examples of the leaving group L in the general formula (II) include halogen atoms, lower alkoxy groups, lower alkylthio groups, lower alkylsulfinyl groups, lower alkylsulfonyl groups, lower alkylsulfonyloxy groups and aryisulfonyloxy groups. Among others, halogen atoms such as fluorine and chlorine are preferred.

This reaction may be carried out by stirring a mixture of the compound (II) and the compound (III) in an inert solvent at a temperature of 10 to 180° C. and preferably 20 to 130° C., for a period of time ranging from 10 minutes to 24 hours and preferably from 30 minutes to 3 hours. Useful solvents include water, methanol, ethanol, acetonitrile, chloroform, pyridine, dimethylformamide, dimethyl sulfoxide, 1-methyl-2-pyrrolidone and the like. These solvents may be used alone or in admixture.

This reaction is generally carried out in the presence of an acid acceptor by using the compound (III) in an amount equivalent to or slightly in excess of that of the compound (II). The compound (III) may be used in excess so as to function as an acid acceptor too. Preferred examples of the acid acceptor include organic bases such as triethylamine, 1,8-diazabicyclo[5.4.0]-7-undecene (DBU), pyridine, quinoline and picoline; and inorganic bases such as sodium hydroxide, potassium hydroxide, sodium carbonate, potassium carbonate, sodium hydrogen carbonate and potassium hydrogen carbonate.

Compounds (II) are well known or may be prepared according to well-known processes. Bicyclic amine compounds (III) are all novel and the processes for the preparation thereof will be described later.

(b) Hydrolysis Reaction

Of the compounds (I) of the present invention, those in carboxylic acid form may also be prepared by hydrolyzing a compound of the general formula (IV)

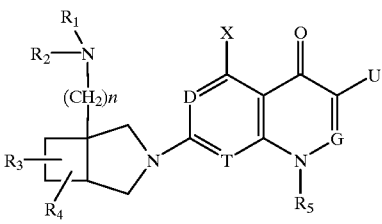

(IV)

wherein U represents a group which can be converted into a carboxyl group by hydrolysis, and $R_1$, $R_2$, $R_3$, $R_4$, $R_5$, n, G, T, X and D have the same meanings as described previously.

In this case, examples of the group U convertible into a carboxyl group include an ester group, a cyano group, an amido group, an amidino group, and a group of the formula —C(=NH)—O— (lower alkyl).

The above hydrolysis reaction may be carried out by bringing the aforesaid compound (IV) into contact with water in a suitable solvent. In order to accelerate this reaction, it is usually carried out in the presence of a catalyst such as an acid or a base. Usable acid catalysts include inorganic acids such as hydrochloric acid, hydrobromic acid, sulfuric acid and phosphoric acid; and organic acids such as acetic acid, trifluoroacetic acid, formic acid and p-toluenesulfonic acid. Usable base catalysts include metal hydroxides such as sodium hydroxide and barium hydroxide; carbonates such as sodium carbonate and potassium carbonate; and sodium acetate.

Usually, water is used as the solvent. However, according to the properties of the compound (IV), a water-miscible organic solvent such as ethanol, ethylene glycol dimethyl ether, or dioxane may be used in combination with water. The reaction temperature may usually range from 0 to 150° C. and preferably from 30 to 100° C.

This reaction may also be carried out by heating the compound (IV) directly in the presence of an acid as described above, and then adding water thereto.

(c) Ring Closure Reaction

Furthermore, the compounds (I) of the present invention may also be prepared by subjecting a compound of the general formula (V)

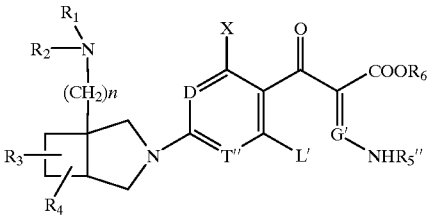

(V)

wherein L' represents a leaving group, $R_5''$ represents a lower alkyl group, a lower alkenyl group, a lower cycloalkyl group, a phenyl group or a heterocyclic group (all of which may further be substituted), G' represents CH or a nitrogen atom, T" represents C—Z or a nitrogen atom in which Z has the same meaning as described previously, $R_6$ represents a lower alkyl group, an allyl group or a benzyl group, and $R_1$, $R_2$, $R_3$, $R_4$, n, X and D have the same meanings as described previously, to a ring closure reaction.

In this case, examples of the leaving group L' include the same groups as described previously for the leaving group L. Among others, halogen atoms such as fluorine and chlorine are preferred.

This ring closure reaction may be carried out by stirring a mixture of the compound (V) and a solvent at a temperature of 30 to 150° C. and preferably 30 to 100° C. for a period of time ranging from 1 to 6 hours in the presence of a base (e.g., potassium carbonate, sodium carbonate, sodium hydride, potassium t-butoxide or potassium fluoride) which is used in an amount of 1 to 3 moles per mole of the compound (V). Preferred examples of the solvent include ethanol, dioxane, tetrahydrofuran, dimethylformamide and dimethyl sulfoxide.

The compound (V) used as the starting material is also novel, and this may be prepared, for example, according to the following reaction formula (1).

presence of a catalyst. Thus, there can be obtained a compound of the present invention in which the amino-protecting group has been converted into a hydrogen atom. The catalysts which can be used in this reaction include, for example, platinum, palladium and Raney nickel catalyst. Usable solvents include, for example, ethylene glycol, dioxane, dimethylformamide, ethanol, acetic acid and water. This reaction may be carried out at a temperature of 60° C. or below and is usually carried out at room temperature.

When the easily hydrogenolyzable amino-protecting group is benzyl, trityl, benzyloxycarbonyl or p-toluenesulfonyl and the like, the protecting group may be eliminated by metallic sodium treatment in liquid ammonia at a temperature of −50 to −20° C.

Reaction formula (1)

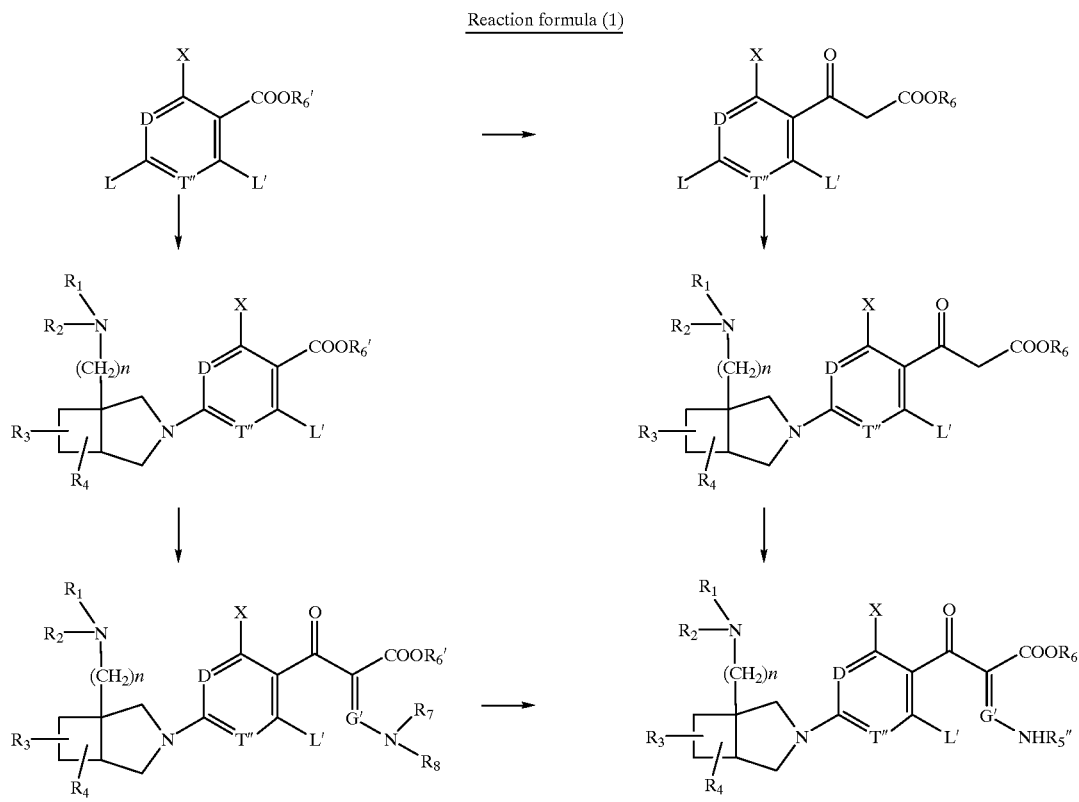

wherein $R_6'$ is a hydrogen atom or has the same meaning as described previously for $R_6$, $R_7$ and $R_8$ may be the same or different and each represents a lower alkyl group, and $R_1$, $R_2$, $R_3$, $R_4$, $R_5''$, $R_6$, n, G', T'', D, X, L and L' have the same meanings as described previously.

When the compound (I) of the present invention prepared according to any of the above-described processes (a), (b) and (c) has an amino-protecting group, it may be subjected to a hydrolysis reaction or a hydrogenolysis reaction as desired. Thus, there can be obtained a compound (I) of the present invention in which the amino-protecting group has been converted into a hydrogen atom.

The reaction for eliminating the amino-protecting group by hydrolysis may be carried out in the same manner as described in the above process (b).

Alternatively, the reaction for eliminating the amino-protecting group by hydrogenolysis may advantageously carried out by treating a compound (I) of the present invention having an easily hydrogenolyzable amino-protecting group with hydrogen gas in a solvent in the The compound (III) used as the starting material in the above-described process (a) may be prepared by treating a compound of the general formula (VI)

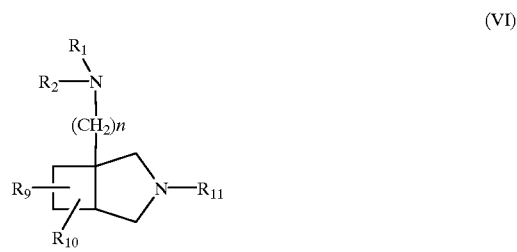

(VI)

wherein $R_9$ and $R_{10}$ have the same meanings as described previously for $R_3$ and $R_4$, or represent groups convertible into $R_3$ and $R_4$, $R_{11}$ represents an amino-protecting group, and $R_1$, $R_2$ and n have the same meanings as described previously, so as to eliminate the amino-protecting group $R_{11}$ and convert it into a hydrogen atom; and when $R_9$ and/or $R_{10}$ are groups convertible into $R_3$ and/or $R_4$, converting $R_9$ and/or $R_{10}$ into $R_3$ and/or $R_4$.

In this case, examples of the amino-protecting group $R_{11}$ include the above-described easily hydrogenolyzable amino-protecting groups and easily hydrolyzable amino-protecting groups. When $R_1$ or $R_2$ in the compound (VI) is an amino-protecting group, it is desirable for subsequent reactions to employ, for $R_{11}$ an amino-proecting group differing in character from the amino-protecting group represented by $R_1$ or $R_2$. For example, when the amino-protecting group represented by $R_1$ or $R_2$ is an easily hydrolyzable amino-protecting group such as t-butoxycarbonyl, an easily hydrogenolyzable amino-protecting group such as benzyl or trityl is preferably chosen for $R_{11}$.

This elimination reaction may be carried out by subjecting the compound (VI) to a hydrogenolysis or hydrolysis reaction which has previously been explained.

With regard to $R_9$ and $R_{10}$, examples of the "groups convertible into $R_3$ and $R_4$" include methanesulfonyloxy, p-toluenesulfonyloxy, benzyloxy, carboxyl, carbamoyl, hydroxyiminomethyl, benzylidene, cyclic acetal and dithioacetal.

Methanesulfonyloxy and p-toluenesulfonyloxy may be converted, by a nucleophilic substitution reaction, into a halogen atom, a cyano group or a lower alkoxy group as used for $R_3$ or $R_4$.

Benzyloxy may be converted into a hydroxyl group as used for $R_3$ or $R_4$, by a hydrogenolysis reaction or a hydrolysis reaction. Carboxyl may be converted into a halogen atom as used for $R_3$ or $R_4$, by deriving an acid halide therefrom and then treating it with the Wilkinson catalyst $\{RhCl[P(C_6H_5)_3]_3\}$.

Furthermore, carbamoyl and hydroxyiminomethyl may be converted into a cyano group as used for $R_3$ or $R_4$, by treatment with thionyl chloride or chlorosulfonyl isocyanate. Benzylidene, cyclic acetal and dithioacetal may be converted into an oxo group as used for $R_3$ or $R_4$, by an oxidation reaction, a hydrolysis reaction using an acid catalyst and a hydrolysis reaction in the presence of mercuric chloride, respectively.

Compounds (VI) are also novel and may be prepared, for example, according to the processes described in Examples I to III which will be given later or processes equivalent thereto.

The compounds (I) of the present invention and the intermediate compounds (III) thereof, which have been prepared in the above-described manner, may be isolated and purified according to any conventional procedure. These compounds are obtained in the form of salts, free acids or amines, or hydrates, depending on the conditions of isolation and purification. According to the intended purposes, these forms may be converted into each other to obtain the compounds of the present invention in desired forms.

The stereoisomers of the compounds (I) and (III) of the present invention may be separated from each other by any conventional method such as fractional crystallization or chromatography. Their optical isomers may be isolated by an optical resolution method which is known per se.

The compounds (I) of the present invention and salts thereof, which have been obtained in the above-described manner, are all novel compounds and are valuable as antibacterial agents because of their high antibacterial activities. The compounds (I) of the present invention and salts thereof can be used not only as drugs for human beings and animals, but also as fish drugs, agricultural chemicals and food preservatives.

Esters of the compounds (I) of the present invention are valuable as raw materials for the synthesis of the compounds (I) of the present invention in carboxylic acid form. However, if these esters themselves may readily be converted into the corresponding carboxylic acids in the body, they exhibit the same action and effect as the carboxylic acids and are hence useful as antibacterial agents.

Moreover, the compounds (III) of the present invention are useful as direct intermediates for the synthesis of the compounds (I) of the present invention.

BEST MODE FOR CARRYING OUT THE INVENTION

Now, the in vitro and in vivo antibacterial activities of the compounds (I) of the present invention are described with reference to the following experimental data. The results are summarized in Table 1. The figures given in this table indicate minimum inhibitory concentrations (MIC; $\mu$g/ml) as measured according to the procedure described in Chemotherapy, 29(1), 76 (1981), and the figures given in brackets indicate effects ($ED_{50}$; mg/kg) on systemic infection in mice.

The effects ($ED_{50}$; mg/kg) on systemic infection in mice were determined as follows: Male Std-ddy strain mice (weighing about 20 g) were infected with each of the pathogenic bacteria shown in Table 1 by administering $5 \times 10^3$ viable microorganisms intraperitoneally to each mouse. Then, a suspension of each test compound in 0.4% carboxymethylcellulose was orally administered twice, i.e., immediately after infection and 6 hours after infection. Seven days after infection, the $ED_5$ value was calculated from the survival rate of each mouse group by probit analysis.

As reference compounds, there were used pipemidic acid that is an excellent antibacterial agent currently on the market, and 7-(1-amino-3-azabicyclo-[3.1.0]hex-3-yl)-1-cyclopropyl-6,8-difluoro-1,4-dihydro-4-oxoquinoline-3-carboxylic acid that has the following structure and is disclosed in Example 6 of the aforementioned Japanese Patent Application Laid-Open No. 56673/'89.

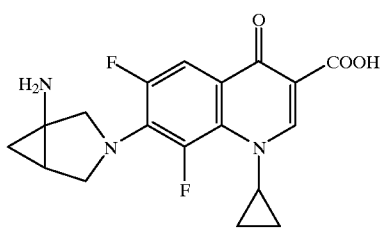

TABLE 1

Antibacterial activities

[Structure: quinolone core with X, F, COOH, T, N-R5, and amino-substituted azabicyclic amine]

| Example No. | R5 | X | T | Salt | Staphylococcus aureus 50774 | Pseudomonas aeruginosa No. 12 |
|---|---|---|---|---|---|---|
| 1 | cyclopropyl | H | CF | — | 0.025 [0.928] | 0.39 [2.00] |
| 2 | cyclopropyl | H | C—Cl | $CF_3CO_2H$ | 0.013 [0.682] | 0.39 [4.28] |
| 3 | cyclopropyl | H | C—OMe | $CF_3CO_2H$ | 0.013 [1.41] | 0.78 [8.62] |
| 4 | cyclopropyl | H | CH | $CF_3CO_2H$ | 0.1 [4.42] | 0.78 [6.92] |
| 5 | cyclopropyl | $NH_2$ | CF | $CF_3CO_2H$ | 0.025 [1.16] | 0.39 [5.08] |
| 6 | cyclopropyl | F | CF | — | 0.05 [4.81] | 1.56 — |
| 7 | Ph—$F_2$ | | H | CH | — | 0.05 [2.25] | 1.56 — |
| 8 | Ph—$F_2$ | | H | N | $CF_3CO_2H$ | 0.05 [0.799] | 0.39 [3.25] |
| 9 | cyclopropyl | H | N | — | 0.05 [1.18] | 0.78 [4.88] |
| 12 | fluorocyclopropyl | H | C—OMe | HCl | 0.013 [2.32] | 0.78 — |
| Reference compound | | | Compound of Example 6 of Japanese Patent Application Laid-Open No. 56673/'89 | | 0.025 [6.82] | 0.1 [12.5] |
| | | | Pipemidic acid | | 12.5 [215] | 12.5 [70.8] |

Ph—$F_2$: 2,4-difluorophenyl; Me: methyl

As shown in Table 1 above, the compounds (I) of the present invention exhibit an excellent antibacterial activity not only in vitro but also in animal experiments. Especially in the in vivo experiments, the compounds of the present invention exhibit a more excellent antibacterial activity than the reference compounds.

The compounds (I) of the present invention have low toxicity and can hence be used as antibacterial agents for the prophylaxis and treatment of bacterial diseases in mammals including man.

When the compounds (I) of the present invention are used as antibacterial agents in human beings, their dosage may vary according to the age and body weight of the patient, the severity of symptoms, the route of administration, and the like. However, it is recommended to administer them in a daily dose of 5 mg to 5 g which may be given once or in several divided doses. The route of administration may be either oral or parenteral.

The compounds (I) of the present invention, may be administered alone to human beings and other mammals. However, they are usually combined with one or more pharmaceutically acceptable additives and administered in the form of pharmaceutical preparations. Such pharmaceutical preparations include tablets, solutions, capsules, granules, powders, syrups, injections, ointments and the like. These pharmaceutical preparations may be made in the usual manner by using common additives. For example, as additives for oral preparations, there may be used various carriers or diluents which are commonly used in the field of pharmaceutics and do not react with the compounds (I) of the present invention, such as starch, mannitol, crystalline cellulose, carboxymethylcellulose calcium, water and ethanol. Moreover, as additives for injections, there may be used various additives which are commonly used in the field of injections, such as water, physiological saline, glucose solutions and transfusions.

The aforesaid solutions and ointments may also be used for purposes of therapy and treatment in the fields of otorhinolaryngology and ophthalmology.

The present invention is further illustrated by the following examples. Examples I to III relate to the preparation of intermediates (III), Examples 1 to 16 relate to the preparation of desired compounds (I), and Example A relates to a pharmaceutical preparation.

EXAMPLE I 1-(t-Butoxycarbonylamino)-3-azabicyclo[3.2.0] heptane (A) 35.1 g of 1-cyclobutene-1-carboxylic acid (J. Chem. Soc., p. 3002, 1953) was dissolved in 250 ml of methylene chloride, and a solution of diphenyldiazomethane in methylene chloride was added dropwise thereto at room temperature until a red color did not disappear any longer. After this mixture was stirred at room temperature for one hour, the dichloromethane was distilled off. To the resulting crude product were added 750 ml of tetrahydrofuran, 93.4 g of N-benzyl-N-(methoxymethyl)trimethylsilylmethylamine (Chem. Pharm. Bull., Vol. 33, p. 2762, 1985), 10.9 g of cesium fluoride and 15.9 g of trimethylsilyl triflate, followed by heating at 60° C. for 18 hours. The reaction mixture was cooled to 0° C., and 350 ml of a 15% aqueous solution of sodium hydroxide was added dropwise thereto, followed by stirring at that temperature for 30 minutes. After the organic layer was separated and dried (over anhydrous magnesium sulfate), the solvent was distilled off under reduced pressure. The resulting residue was purified by silica gel column chromatography (using a 30:1 mixture of n-hexane and ethyl acetate as the eluent) and recrystallization (from diisopropyl ether) to obtain 52.1 g of 3-benzyl-1-diphenylmethoxycarbonyl- 3-azabicyclo[3.2.0]heptane.

Melting point: 96–99° C. $^1$H-NMR (CDCl$_3$), δ: 1.69–2.32 (m, 4H), 2.40–3.50 (m, 5H), 3.71 (s, 2H), 6.87 (s, 1H), 7.17–7.44 (m, 15H); IR (KBr), cm$^{-1}$: 1720; MS (m/z): 398 (MH$^+$)

(B) 45.8 g of the compound obtained in the preceding step (A) and 92 ml of a 20% aqueous solution of sodium hydroxide were added to 700 ml of methanol, followed by heating under reflux for 5 hours. After cooling, this mixture was neutralized by the addition of 20% hydrochloric acid, and concentrated under reduced pressure. After the addition of water and diisopropyl ether, the resulting mixture was vigorously stirred and the aqueous phase was separated. After this aqueous layer was continuously extracted with chloroform, the extract was dried (over anhydrous magnesium sulfate) and the chloroform was distilled off. The resulting crude product was dissolved in 450 ml of t-butanol, and 88.2 g of diphenylphosphoryl azide (DPPA) and 32.4 g of triethylamine were added thereto, followed by heating under reflux for 15 hours. The reaction mixture was concentrated under reduced pressure, mixed with ethyl acetate, and washed twice with a 10% aqueous solution of sodium hydroxide. The organic layer was dried (over anhydrous magnesium sulfate) and then concentrated under reduced pressure. The resulting residue was purified by silica gel column chromatography (using a 9:1 mixture of n-hexane and ethyl acetate as the eluent) and recrystallization (from n-hexane) to obtain 17.6 g of 3-benzyl-1-(t-butoxycarbonylamino)-3-azabicyclo[3.2.0]heptane.

Melting point: 69–70° C. $^1$H-NMR (CDCl$_3$), δ: 1.42 (s, 9H), 1.50–1.77 (m, 1H), 2.03–2.45 (m, 5H), 2.60–2.80 (m, 1H), 2.73 (d, 1H, J=9 Hz), 3.01 (d, 1H, J=9 Hz), 3.68 (s, 2H), 4.73 (br s, 1H), 7.19–7.41 (m, 5H); IR (KBr), cm$^{-1}$: 3380, 1685; MS (m/z): 303 (MH$^+$)

(C) 5 g of the compound obtained in the preceding step (B) was dissolved in 100 ml of ethanol, and 1 g of 10% palladium-carbon was added thereto. Then, a stoichiometric amount of hydrogen was added thereto. After the catalyst was separated by filtration, the solvent was distilled off. The resulting crude crystals were recrystallized from n-hexane-diisopropyl ether to obtain 3 g of 1-(t-butoxycarbonylamino)-3-azabicyclo[3.2.0]heptane.

Melting point: 113–116° C. $^1$H-NMR (CDCl$_3$), δ: 1.25–1.41 (m, 1H), 1.45 (s, 9H), 1.96–2.35 (m, 4H), 2.65–2.87 (m, 3H), 2.95–3.15 (m, 2H), 4.82 (br, 1H); IR (KBr), cm$^{-1}$: 3294, 3185, 2982, 1692; MS (m/z): 213 (MH$^+$)

EXAMPLE II

1-Methylamino-3-azabicyclo[3.2.0]heptane (A) 6.8 g of 3-benzyl-1-(t-butoxycarbonylamino)-3-azabicyclo[3.2.0]heptane was dissolved in 20 ml of methylene chloride, and 50 ml of trifluoroacetic acid was added thereto, followed by stirring for 3 hours. The reaction mixture was concentrated, mixed with an aqueous solution of sodium hydroxide under cooling with ice, and extracted with chloroform. After the extract was dried over anhydrous magnesium sulfate, the chloroform was distilled off. The resulting crude product was dissolved in 47 ml of formic acid, and 17 g of acetic anhydride was added dropwise thereto, under cooling with ice, over a period of 90 minutes. After the addition of ice water, the resulting mixture was neutralized by the addition of an aqueous solution of sodium hydroxide under cooling with ice, and extracted with ethyl acetate. The organic layer was dried over anhydrous magnesium sulfate and then concentrated under reduced pressure. The resulting residue was purified by silica gel column chromatography (using a 30:1 mixture of chloroform and methanol as the eluent) to obtain 3.1 g of 3-benzyl-1-formylamino-3-azabicyclo[3.2.0]heptane.

$^1$H-NMR (CDCl$_3$), δ: 1.61–1.82 (m, 1H), 2.08–2.50 (m, 5H), 2.61–3.14 (m, 3H), 3.69 (s, 2H), 5.90 (br, 1H), 7.18–7.42 (m, 5H), 8.05 (d, 1H, J=2 Hz); IR (neat), cm$^{-1}$: 3270, 3028, 2940, 2791, 1659, 1530; MS (m/z): 231 (MH$^+$)

(B) 3.1 g of the compound obtained in the preceding step (A) was dissolved in 30 ml of toluene, and 20 ml of a 70% solution of sodium bis(2-methoxyethoxy)aluminum hydride in toluene was added thereto, followed by heating under reflux for 2 hours. After cooling, the reaction mixture was slowly added to 20% sulfuric acid under cooling with ice, and the insoluble matter was separated by filtration. The filtrate was adjusted to pH 11 by the addition of a 20% aqueous solution of sodium hydroxide, and then extracted with chloroform. After the extract was dried over anhydrous magnesium sulfate, the solvent was distilled off under reduced pressure. The resulting residue was purified by silica gel column chromatography (using a 100:1 mixture of n-hexane and ethyl acetate as the eluent) to obtain 1.97 g of 3-benzyl-1-methylamino-3-azabicyclo[3.2.0]heptane.

$^1$H-NMR (CDCl$_3$), δ: 1.40–1.72 (m, 2H), 1.89–2.55 (m, 6H), 2.33 (s, 3H), 2.79 (d, 1H, J=20 Hz), 2.83 (d, 1H, J=20 Hz), 3.66 (s, 2H), 7.18–7.43 (m, 5H); IR (neat), cm$^{-1}$: 3270, 2937, 2788; MS (m/z): 217 (MH$^+$), 187

(C) 1.95 g of the compound obtained in the preceding step (B) was dissolved in 30 ml of ethanol, and 0.4 g of 10% palladium-carbon and 2 ml of concentrated hydrochloric acid were added thereto. Then, a stoichiometric amount of hydrogen was added thereto at 50° C. The catalyst was separated by filtration and washed with methanol. After the solvent was distilled off, the resulting residue was adjusted to pH 11 by the addition of an aqueous solution of sodium hydroxide, and then extracted with chloroform. After the extract was dried over anhydrous magnesium sulfate, the solvent was distilled off under reduced pressure to obtain 0.96 g of 1-methylamino-3-azabicyclo[3.2.0]heptane.

$^1$H-NMR (CDCl$_3$), δ: 1.21–1.45 (m, 1H), 1.77–3.00 (m, 10H), 2.38 (s, 3H); IR (neat), cm$^{-1}$: 3270, 2942, 1692

EXAMPLE III 1-(t-Butoxycarbonylaminomethyl)-3-azabicyclo[3.2.0]-heptane (A) 13 g of 3-benzyl-1-diphenylmethoxycarbonyl-3-azabicyclo[3.2.0]heptane was dissolved in 100 ml of tetrahydrofuran, and 2.8 g of lithium chloride was added thereto. After 2.5 g of sodium borohydride was added little by little, 30 ml of methanol was slowly added thereto and the resulting mixture was stirred at room temperature for 15 hours. The reaction mixture was concentrated under reduced pressure, mixed with ice water, and extracted with ethyl acetate. After the extract was mixed with 10% hydrochloric acid and stirred vigorously, the aqueous layer was separated. This aqueous layer was adjusted to pH 8 by the addition of a 10% aqueous solution of sodium hydroxide, and then extracted with ethyl acetate. After the extract was dried over anhydrous magnesium sulfate, the solvent was distilled off under reduced pressure. The resulting residue was purified by silica gel column chromatography (using a 4:1 mixture of n-hexane and acetone as the eluent) to obtain 5.4 g of 3-benzyl-1-hydroxymethyl-3-azabicyclo[3.2.0]heptane.

1H-NMR (CDCl$_3$), δ: 1.64–2.19 (m, 6H), 2.28–2.80 (m, 4H), 3.52–3.77 (m, 4H), 7.18–7.43 (m, 5H); IR (neat), cm$^{-1}$: 3346, 2934, 2785; MS (m/z): 218 (MH$^+$)

(B) 5.3 g of the compound obtained in the preceding step (A) was dissolved in 200 ml of tetrahydrofuran, and 7.1 g of triphenylphosphine, 5.2 g of diethyl azodicarboxylate and 7.4 g of diphenylphosphoryl azide were successively added thereto, followed by stirring at room temperature for 48 hours. After the reaction mixture was concentrated under reduced pressure, ethyl acetate and 10% hydrochloric acid were added thereto. The resulting mixture was vigorously stirred and the aqueous phase was separated. This aqueous layer was adjusted to pH 11 by the addition of a 20% aqueous solution of sodium hydroxide, and then extracted with chloroform. After the extract was dried over anhydrous magnesium sulfate, the solvent was distilled off under reduced pressure. The resulting residue was purified by silica gel column chromatography (using a 30:1 mixture of n-hexane and ethyl acetate as the eluent) to obtain 5.4 g of 1-azidomethyl-3-benzyl-3-azabicyclo[3.2.0]-heptane.

$^1$H-NMR (CDCl$_3$), δ: 1.65–2.26 (m, 6H), 2.39–2.52 (m, 1H), 2.80 (d, 1H, J=9 Hz), 2.81 (d, 1H, J=9 Hz), 3.37 (d, 1H, J=20 Hz), 3.43 (d, 1H, J=20 Hz), 3.64 (d, 1H, J=16.5 Hz), 3.71 (d, 1H, J=16.5 Hz), 7.18–7.44 (m, 5H); IR (neat), cm$^{-1}$: 2937, 2787, 2096; MS (m/z): 243 (MH$^+$)

(C) 3.4 g of the compound obtained in the preceding step (B) was dissolved in 70 ml of tetrahydrofuran, and 5.9 g of triphenylphosphine was added thereto, followed by stirring at 50° C. for 2 hours. Then, 55 ml of a 28% aqueous solution of ammonia was added thereto, followed by stirring at 50° C. for 3 hours. The organic layer was separated and the aqueous layer was extracted with diethyl ether. After 1N hydrochloric acid was added to the combined organic layers, the resulting mixture was vigorously stirred and the aqueous phase was separated. This aqueous layer was adjusted to pH 11 by the addition of a 10% aqueous solution of sodium hydroxide, and then extracted with methylene chloride. After the extract was dried over anhydrous magnesium sulfate, the solvent was distilled off under reduced pressure. The resulting residue was dissolved in 100 ml of tetrahydrofuran. Then, 7.7 g of di-t-butyl dicarbonate was added thereto, followed by stirring at room temperature for 15 hours. After the reaction mixture was concentrated under reduced pressure, the resulting residue was purified by silica gel column chromatography (using a 9:1 mixture of n-hexane and ethyl acetate as the eluent) and recrystallization (from n-hexane) to obtain 3.92 g of 3-benzyl-1-(t-butoxycarbonylaminomethyl)-3-azabicyclo[3.2.0]heptane.

Melting point: 78–79° C. $^1$H-NMR (CDCl$_3$), δ: 1.44 (s, 9H), 1.64–2.47 (m, 7H), 2.72 (d, 1H, J=9 Hz), 2.74 (d, 1H, J=9 Hz), 3.20 (dd, 1H, J=23 Hz, 6 Hz), 3.28 (dd, 1H, J=23 Hz, 6 Hz); IR (KBr), cm$^{-1}$: 3372, 2972, 2932, 2797, 1688, 1530; MS (m/z): 317 (MH$^+$), 259

(D) 2.9 g of the compound obtained in the preceding step (C) was dissolved in 60 ml of ethanol, and 0.6 g of 10% palladium-carbon was added thereto. Then, a stoichiometric amount of hydrogen was added thereto at 50° C. After the catalyst was separated by filtration, the solvent was distilled off. The resulting crude crystals were recrystallized from n-hexanediisopropyl ether to obtain 1.58 g of 1-(t-butoxycarbonylaminomethyl)-3-azabicyclo[3.2.0]heptane.

Melting point: 83–86° C. IR (KBr), cm$^{-1}$: 3311, 3192, 2960, 1720, 1556

EXAMPLE 1

7-(1-Amino-3-azabicyclo[3.2.0]hept-3-yl)-1-cyclopropyl-6,8-difluoro-1,4-dihydro-4-oxoquinoline-3-carboxylic acid (A) 1.9 g of 1-(t-butoxycarbonylamino)-3-azabicyclo[3.2.0]heptane and 0.83 g of 1-cyclopropyl-6,7,8-trifluoro-1,4-dihydro-4-oxoquinoline-3-carboxylic acid were added to 15 ml of pyridine, followed by heating under reflux for 4 hours. After the solvent was distilled off under reduced pressure, the resulting residue was purified by silica gel column chromatography (using a 100:1 mixture of chloroform and methanol as the eluent) and recrystallization (from ethyl acetate-diisopropyl ether) to obtain 0.99 g of 7-[1-(t-butoxycarbonylamino)-3-azabicyclo[3.2.0]hept-3-yl]-1-cyclopropyl-6,8-difluoro-1,4-dihydro-4-oxoquinoline-3-carboxylic acid (m.p. 211–215° C.).

(B) 0.97 g of the compound obtained in the preceding step (A) was dissolved in 20 ml of a 35% solution of hydrogen chloride in ethanol, and this solution was heated at 80° C. for 10 minutes. After the reaction solution was concentrated under reduced pressure, acetonitrile and diethyl ether were added thereto, and the formed crystals were collected by filtration. These crystals were purified by CHP-20P column chromatography (using a 7:3 mixture of water and acetonitrile as the eluent) to obtain 244 mg of the desired product [m.p. 242–247° C. (dec.)].

EXAMPLE 2

7-(1-Amino-3-azabicyclo[3.2.]hept-3-yl)-8-chloro-1-cyclopropyl-6-fluoro-1,4-dihydro-4-oxoquinoline-3-carboxylic acid trifluoroacetate (A) 1.22 g of 1-(t-butoxycarbonylamino)-3-azabicyclo[3.2.0]heptane, 0.96 g of 8-chloro-1-cyclopropyl-6,7-difluoro-1,4-dihydro-4-oxoquinoline-3-carboxylic acid and 0.58 g of 1,8-diazabicyclo[5.4.0]-7-undecene were added to 20 ml of acetonitrile, followed by heating under reflux for 3.5 hours. After the solvent was distilled off under reduced pressure, the resulting residue was purified by silica gel column chromatography (using a 100:1 mixture of chloroform and methanol as the eluent) and recrystallization (from ethyl acetate-diisopropyl ether) to obtain 0.96 g of 7-[1-(t-butoxycarbonylamino)-3-azabicyclo[3.2.0]hept-3-yl]-8-chloro-1-cyclopropyl-6-fluoro-1,4-dihydro-4-oxoquinoline-3-carboxylic acid (m.p. 200–202° C.).

(B) 0.94 g of the compound obtained in the preceding step (A) was dissolved in 10 ml of methylene chloride, and 20 ml of trifluoroacetic acid was added thereto, followed by stirring at room temperature for 15 hours. After the reaction mixture was concentrated under reduced pressure, acetonitrile and diethyl ether were added thereto and the formed crystals were collected by filtration. These crystals were washed with acetonitrile to obtain 650 mg of the desired product [m. p. 236–240° C. (dec.)].

EXAMPLE 3

7-(1-Amino-3-azabicyclo[3.2.0]hept-3-yl)-1-cyclopropyl-6-fluoro-1,4-dihydro-8-methoxy-4-oxoquinoline-3-carboxylic acid trifluoroacetate (A) 1.07 g of 1-(t-butoxycarbonylamino)-3-azabicyclo[3.2.0]heptane, 1.15 g of 1-cyclopropyl-6,7-difluoro-1,4-dihydro-8-methoxy-4-oxoquinoline-3-carboxylic acid-$BF_2$ chelate and 0.68 g of triethylamine were added to 18 ml of dimethyl sulfoxide, followed by stirring at room temperature for 16 hours. After the addition of water, the resulting mixture was extracted with chloroform and the solvent was distilled off. To the resulting residue were added 300 ml of 80% ethanolwater and 50 ml of triethylamine, followed by heating under reflux for 3 hours. After the reaction mixture was concentrated under reduced pressure, the residue was mixed with water and extracted with chloroform. After the extract was dried over anhydrous magnesium sulfate, the solvent was distilled off. The resulting residue was purified by silica gel column chromatography (using a 100:1 mixture of chloroform and methanol as the eluent) and recrystallization (from ethyl acetate-diisopropyl ether) to obtain 1.17 g of 7-[1-(t-butoxycarbonylamino)-3-azabicyclo[3.2.0]hept-3-yl]-1-cyclopropyl-6-fluoro-1,4-dihydro-8-methoxy-4-oxoquinoline-3-carboxylic acid (m.p. 211–213° C.).

(B) The compound obtained in the preceding step (A) was treated in the same manner as described in step (B) of Example 2 to obtain the desired product [m.p. 230–235° C. (dec.)].

EXAMPLES 4–11

The compounds shown in Table 2 below were obtained by carrying out reaction and treatment in the same manner as described in Example 2.

TABLE 2

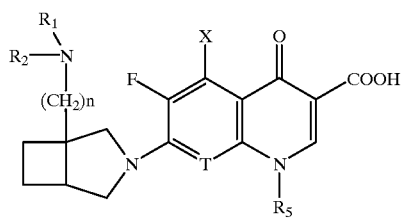

| Example No. | | $R_1$ | $R_2$ | n | $R_5$ | X | T | Salt | Melting Point (° C.) |
|---|---|---|---|---|---|---|---|---|---|
| 4 | A | Boc | H | 0 |  | H | CH | — | 234–236 |
|  | B | H | H |  |  |  |  | $CF_3CO_2H$ | 255–260 (dec.) |
| 5 | A | Boc | H | 0 |  | $NH_2$ | CF | — | 229–231 |
|  | B | H | H |  |  |  |  | $CF_3CO_2H$ | 250–257 (dec.) |

TABLE 2-continued

| Example No. | | $R_1$ | $R_2$ | n | $R_5$ | X | T | Salt | Melting Point (° C.) |
|---|---|---|---|---|---|---|---|---|---|
| 6 | A | Boc | H | 0 | cyclopropyl | F | CF | — | 230–235 |
|   | B | H | H |   |   |   |   | — | 272–275 (dec.) |
| 7 | A | Boc | H | 0 | Ph-F$_2$ | H | CH | — | 147–150 |
|   | B | H | H |   |   |   |   | — | 216–218 |
| 8 | A | Boc | H | 0 | Ph—F$_2$ | H | N | — | 131–134 |
|   | B | H | H |   |   |   |   | CF$_3$CO$_2$H | 219–222 |
| 9 | A | Boc | H | 0 | cyclopropyl | H | N | — | 247–250 |
|   | B | H | H |   |   |   |   | CF$_3$CO$_2$H | 261–267 (dec.) |
| 10 | A | H | H | 0 | t-Bu | H | N | — | 245–253 (dec.) |
| 11 | A | Boc | H | 0 | cyclopropyl | NH$_2$ | CH | — | 210–215 (dec.) |
|    | B | H | H |   |   |   |   | CF$_3$CO$_2$H | 231–235 (dec.) |

Boc: t-butoxycarbonyl; Ph—F$_2$: 2,4-difluorophenyl
Me: methyl; t-Bu: t-butyl

EXAMPLE 12–16

The compounds shown in Table 3 below were obtained by carrying out reaction and treatment in the same manner as described in Example 3.

TABLE 3

| Example No. | | $R_1$ | $R_2$ | n | X | $R_5$ | T | Salt | Melting Point (° C.) |
|---|---|---|---|---|---|---|---|---|---|
| 12 | A | Boc | H | 0 | H | fluorocyclopropyl | C—OMe | — | Non-crystalline |
|    | B | H | H |   |   |   |   | HCl | 218–223 (dec.) |

TABLE 3-continued

[Structure shown with R1, R2, N, (CH2)n, F, X, O, COOH, T, N, R5 and cyclobutane-fused pyrrolidine]

| Example No. | R₁ | R₂ | n | X | R₅ | T | Salt | Melting Point (° C.) |
|---|---|---|---|---|---|---|---|---|
| 13 | A | Me | H | 0 | H | [cyclopropyl] | C—OMe | — | 205–207 |
| 14 | A | Boc | H | 1 | H | [cyclopropyl] | C—OMe | — | 188–190 |
|    | B | H   | H |   |   |                |        | HCl | 162–166 |
| 15 | A | Boc | H | 0 | H | [CH₂–O–CH(Me)– (S)] | | HCl | 205–210 |
|    | B | H   | H |   |   |                |        |      | 273–283 (dec.) |
| 16 | A | Boc | H | 0 | H | [cyclopropyl] | C—OCHF₂ | — | 146–152 |
|    | B | H   | H |   |   |                |         | HCl | 237–242 (dec.) |

Boc: t-butoxycarbonyl; Me: methyl

Example A (Formation of Tablets)

| | |
|---|---|
| Compound of Example 1 or 2 | 250 g |
| Corn starch | 54 g |
| Carboxymethylcellulose calcium | 40 g |
| Microcrystalline cellulose | 50 g |
| Magnesium stearate | 6 g |

The above ingredients were blended together with ethanol. The resulting blend was granulated and tableted in the usual manner. Thus, there were obtained 1,000 tablets each weighing 400 mg.

EXPLOITABILITY IN INDUSTRY

As described above, the compounds (I) of the present invention are useful as drugs (antibacterial agents) for mammals including man. Moreover, the compounds (III) of the present invention are useful as direct intermediates for the synthesis of the compounds (I).

We claim:

1. A bicyclic amino group-substituted pyridonecarboxylic acid compound of the general formula (I)

$$A—Pri \quad (I),$$

esters thereof and salts thereof, wherein:

Pri is a pyridonecarboxylic acid residue, and
A is a bicyclic amino group represented by the following formula (C) and joined to the 7-position of the pyridonecarboxylic acid or a position equivalent to the 7-position thereof,

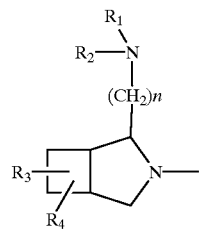

(C)

wherein $R_1$ and $R_2$ may be the same or each represents a hydrogen atom, a lower alkyl group or an amino-protecting group; $R_3$ and $R_4$ each represents a hydrogen atom; and n is an integer of 0 or 1.

2. A bicyclic amino group-substituted pyridonecarboxylic acid compound, esters thereof and salts thereof as claimed in claim 1 wherein Pri is a pyridonecarboxylic acid residue of the formula

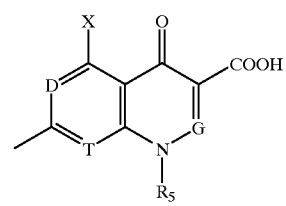

wherein $R_5$ represents a lower alkyl group, a lower alkenyl group, a lower cycloalkyl group, a phenyl group or a heterocyclic group (all of which may further be substituted);

G represents C—E or a nitrogen atom in which E represents a hydrogen atom or combines with $R_5$ to form a bridge represented by the formula —S—CH(CH$_3$)—; T represents C—Z or a nitrogen atom in which Z represents a hydrogen atom, a halogen atom, a cyano group, a lower alkoxy group, a halogenated lower alkoxy group, a lower alkyl group or a halogenated lower alkyl group, or combines with $R_5$ to form a bridge represented by the formula —O—CH$_2$—CH(CH$_3$)—; X represents a hydrogen atom, a halogen atom, a hydroxyl group, a lower alkyl group or an amino group which may be protected; and D represents C—Y or a nitrogen atom in which Y represents a hydrogen atom or a halogen atom.

3. A bicyclic amino group-substituted pyridonecarboxylic acid compound, esters thereof and salts thereof as claimed in claim 2 wherein the bicyclic amino group-substituted pyridonecarboxylic acid compound is represented by the general formula

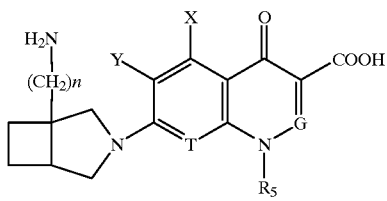

wherein n is an integer of 0 or 1 and $R_5$, G, T, X and Y have the same meanings as described in claim 2.

4. A bicyclic amino group-substituted pyridonecarboxylic acid compound, esters thereof and salts thereof as claimed in claim 3 wherein the bicyclic amino group-substituted pyridonecarboxylic acid compound is represented by the general formula

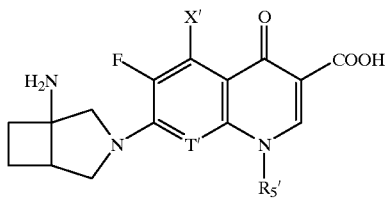

wherein $R_5'$ is a cyclopropyl group which may be substituted by fluorine, a 2,4-difluorophenyl group or a t-butyl group, X' is a hydrogen atom, a halogen atom or an amino group, and T' is CH, CF, CCl, C—OCH$_3$, C—OCHF$_2$ or a nitrogen atom.

5. A bicyclic amine compound of the general formula (III)

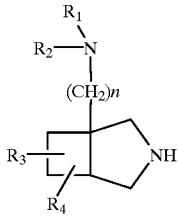

(III)

and salts thereof, wherein $R_1$, $R_2$, $R_3$, $R_4$ and n have the same meanings as described in claim 1.

6. A bicyclic amine compound and salts thereof as claimed in claim 5 wherein all of $R_1$, $R_2$, $R_3$ and $R_4$ are hydrogen atoms and n is 0.

7. An antibacterial composition comprising an effective amount of a bicyclic amino group-substituted pyridonecarboxylic acid compound of the general formula (I)

A—Pri     (I)

wherein Pri and A have the same meanings as described in claim 1, an ester thereof or a salt thereof, and one or more pharmaceutically acceptable additives.

8. A method for the treatment of a bacterial disease in a mammal which comprises administering an effective amount of a bicyclic amino group-substituted pyridonecarboxylic acid compound of the general formula (I)

A—Pri     (I)

wherein Pri and A have the same meanings as described in claim 1, an ester thereof or a salt thereof to the mammal.

* * * * *

UNITED STATES PATENT AND TRADEMARK OFFICE
CERTIFICATE OF CORRECTION

PATENT NO. : 5,990,106
DATED : November 23, 1999
INVENTOR(S) : Masato SAKAMOTO et al.

It is certified that error appears in the above-identified patent and that said Letters Patent is hereby corrected as shown below:

Claim 1, line 10, correct formula (C) to read

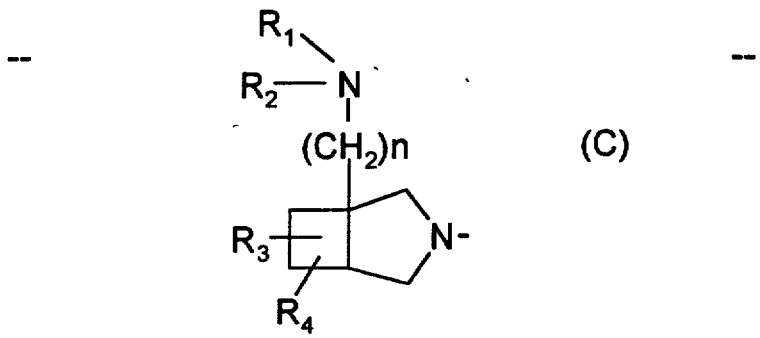

line 11, after "same or" insert --different and--.

Signed and Sealed this

Twelfth Day of September, 2000

Attest:

Q. TODD DICKINSON

*Attesting Officer*           *Director of Patents and Trademarks*